United States Patent [19]

Warren

[11] 4,162,850
[45] Jul. 31, 1979

[54] FIELD TEST FOR SCHISTOSOMA EGGS

[75] Inventor: Kenneth S. Warren, Cleveland, Ohio

[73] Assignee: Case Western Reserve University, Cleveland, Ohio

[21] Appl. No.: 662,790

[22] Filed: Mar. 1, 1976

[51] Int. Cl.$^2$ .................... B01D 13/00; C12K 1/04; G01N 31/00; G01N 33/16

[52] U.S. Cl. .................... 356/38; 23/230 B; 210/23 R; 210/DIG. 23; 356/36; 424/2; 424/3; 935/39; 935/30

[58] Field of Search .................... 424/2, 3, 7; 195/103.5 M, 92; 23/230 B; 210/23 R, DIG. 23; 356/36, 38; 73/53

[56] References Cited

PUBLICATIONS

Wylie, J. Amer. Vet. Med. Asso. vol. 156, May 15, 1970, pp. 1403–1405.
Dennis et al., The J. of Parasitology, vol. 57, Oct. 1971, pp. 1146–1147.
Bradley, Bull. Org. mond. Santé Bull. Wld. Hlth. Org., vol. 33, 1965, pp. 503–508.
Gelman, Membrane Filtration Prod., May 1975, pp. 4, 17.
Millipore-Low Vol. Sterilizing Filtration, Millipore Corp., Bedford, Mass., App. Report AR-11, 1969, pp. 4, 5, 13, 16, 17, 21.
Millipore, Tech. for Microbiol. Analysis, Millipore Corp., Bedford, Mass., ADM-40, pp. 2, 4, 5, 7–9, 12, 15–17, 29, 34, 35.
Gelman Membrane Filtration Products, booklet, Gelman Inst. Co., Ann Arbor, Mich., May 1975, pp. 10, 11, 16, 27.
Bradley, Bull. World Health Org., vol. 33, 1965, p. 33.
Dazo, Bull. World Health Org., vol. 51, 1974, pp. 399–408, as cited in Vet. Bull., vol. 46, 1976, Ab. No. 1431.

*Primary Examiner*—Anna P. Fagelson
*Attorney, Agent, or Firm*—Sprung, Felfe, Horn, Lynch & Kramer

[57] ABSTRACT

Eggs of Schistosoma species in urine are reliably counted in a simple field test involving passing a urine sample of 10 ml or less through a thin transparent microporous membrane having pores of less than about 30 μm, drying the membrane until ready for counting, wetting the membrane with a drop of saline solution, scanning the membrane at about 40X magnification and counting the eggs. Workers of limited skill can run a test in about 1 minute.

2 Claims, No Drawings

FIELD TEST FOR SCHISTOSOMA EGGS

The present invention relates to a test for the presence of eggs of Schistosoma in patients.

Schistosomiasis haematobia is a disease afflicting more than 60 million people in Africa and the Middle East involving worm—or snail-like organisms which cause much general damage and particularly liver damage. The mature worms may range from about 1 to 2 cm and the female may lay as many as a few thousand eggs each day.

Treatment with the drug niridazole will kill the worms but the drug is quite toxic so its use presents certain hazards. Furthermore, there are certain side effects so, for a variety of reasons, administration of the therapeutic should be limited only to those exhibiting high worm egg counts rather than administering the therapeutic indiscriminately to broad populations including even many uninfected patients.

It therefore becomes necessary to have a reliable test for definitely determining the presence of the condition and its intensity. Different procedures are described in the literature. For example, Scott in Texas Reports on Biology & Medicine Vol. 15 (1957) pages 425–430 collected from each suspected infected individual separate urine samples over the course of a day, centrifuged 50 ml samples, spread the solid sediment on a slide, and forwarded the slides to a central laboratory where first one and then a second experienced technician made an egg count. There were sometimes discrepancies which required resolution by a third count by the author or laboratory supervisor.

Similarly Bradley in Bulletin of the World Health Organization, Vol. 33 (1965) 33 discloses an egg counting technique using large opaque filters and requiring staining, and the results are still difficult to read accurately.

Because of the long time for analysis, it meant the patient usually had left and had to return for treatment if the test indicated treatment was warranted. It was often difficult however, to get the patient to return.

It is accordingly an object of the invention to provide a simple, inexpensive test which can be used by technicians with limited skills to determine quickly and accurately, in the field, who of hundreds of tested individuals are afflicted with schistosomiasis, so that treatment can be begun almost immediately after detection if desired.

These and other objects and advantages are realized in accordance with the present invention pursuant to which a relatively small urine sample from each patient is passed through a substantially colorless microporous polymeric membrane having pores smaller than about 30 $\mu$m. The membrane may then be dried whereupon it can be stored even at ambient temperature. If desired, after moistening with even a drop of saline solution to render the eggs visible even without straining, the membranes are examined even at relatively low magnification, e.g. about 40X, and accurate egg counts are obtained in one minute or less.

The urine samples could range from as little as 1 ml up to 10 ml or more and good reproducibility is realized with about 5 ml samples which is a convenient size for working with syringes employed to take up the urine sample and force it through the membrane.

The microporous membranes can comprise any of a variety of polymers but polycarbonate membranes of a thickness of the order of about 10 $\mu$m have proven quite satisfactory, since the egg diameter is about 50 $\mu$m. The pore size may be even smaller, but there is no need to go below 10 $\mu$m. The pores, of course, need not be uniform in size so long as they do not let the eggs pass therethrough. Membrane discs of a diameter of 10 or more mm, e.g. about 10 to 25, especially about 10 to 20 and particularly about 13 mm, are suited for use in filtration and microscopic viewing. At the low magnifications involved, e.g. about 10 to 100X and preferably about 25 to 50X, the whole membrane can be scanned in a few passes and all the eggs counted accurately, without staining, in less than a minute. Where no eggs are present, a determination can take less than 15 seconds.

Comparing results of the test procedure against other techniques and against re-runs shows a high order of reliability and reproducibility. Even using samples as small as 0.1 ml the test results are accurate.

The test procedure is applicable to egg counts for a variety of Schistosoma species, e.g. *Schistosoma haematobium*. It permits large populations to be tested reliably in the field by technicians of limited skill so that those who are found to be afflicted can be treated promptly.

The invention is further described in the following illustrative examples:

EXAMPLE 1

Urine samples were collected in glass bottles or paper cups. Each sample was well mixed by drawing urine in and out of a plastic disposable syringe without a needle. The desired volume of urine was withdrawn (10, 5, 1 ml) and injected through a PT-013 chamber containing a polycarbonate disc 10 $\mu$m thick, 13 mm in diameter and with an average pore size of 8 $\mu$m (Nucleopore Corp., Pleasanton, Ca. 94566). The syringe was removed and filled with air which was injected through the disc in the chamber. The chamber was opened, the disc was removed and placed face down on a glass slide. The dried discs remained attached to the glass slides and were stored in slide boxes until counting was performed. Prior to counting, each disc was moistened with a drop of saline to render the eggs clearly visible. Using 40X magnification each disc was scanned completely in 4 passes and the egg counts were recorded. After each urine sample, the chambers and syringes were washed thoroughly in a solution of detergent (Teepol) followed by two rinses in clear water. Frequent random checks for egg contamination of the syringes or chambers were made by filling the syringes with water and injecting it through fresh discs; eggs were never seen on these preparations.

Urine samples were obtained from individuals living in areas known to be endemic for *Schistosoma haematobium* in Kenya. In one survey, urine samples were examined using 10 or 5 ml in comparison with 1 ml aliquots. Approximately 5% of the 10 and 5 ml aliquots would not pass completely through the discs but this did not occur with any of the 1 ml aliquots.

Table 1 summarizes the results of egg counting using 10 and 1 ml or 5 and 1 ml aliquots. In no case where the 10 or 5 ml samples were negative, were eggs found in the 1 ml sample. When the 10 ml sample contained a range of 1–9 eggs (mean 3.18) or the 5 ml sample contained a range of 1–4 eggs (mean 2.17) all the 1 ml samples examined were negative. When the mean number of eggs in the 10 ml aliquots were greater than 10, the 1 ml aliquots all contained at least 1 egg. Furthermore, when the mean numbers of eggs were adjusted for volume, the differences between the 10 and 1 ml samples were not statistically significant. The results were the same when 5 and 1 ml aliquots were compared.

Table 1

Counts of *Schistosoma haematobium* eggs in different aliquots of urine taken from the same sample 10 ml as compared to 1 ml aliquots

| No. of samples | 10 ml aliquots | | 1 ml aliquots | |
|---|---|---|---|---|
| | interval | mean ± s.e. | interval | mean ± s.e. |
| 63 | 0 | 0 | 0 | 0 |
| 11 | 1–9 | 3.2 ± .74 | 0 | 0 |
| 31 | 10–99 | 39.4 ± 5.48 | 1–14 | 4.2 ± .57 |
| 15 | 100–400 | 166.7 ± 21.08 | 9–35 | 15.3 ± 1.74 |

5 ml as compared to 1 ml aliquouts

| No. of samples | 5 ml aliquots | | 1 ml aliquots | |
|---|---|---|---|---|
| | interval | mean ± s.e. | interval | mean ± s.e. |
| 48 | 0 | 0 | 0 | 0 |
| 12 | 1–4 | 2.2 ± .30 | 0 | 0 |
| 13 | 5–200 | 54.8 ± 16.43 | 1–36 | 8.9 ± 3.14 |

EXAMPLE 2

In a second survey 390 patients were examined. Two aliquots of 5 ml each were injected through the discs to test the reproducibility of the test. The test procedure was otherwise as described in Example 1.

The discs in each aliquot were identified as A and B, the egg count results were placed into different egg-count intervals, and the mean egg count within each interval was calculated. As can be seen in Table II, the mean counts were similar within each interval, and paired "t" tests revealed no statistical differences between the two sets of counts. The same data, presented in a different form in Table III, reveals that the great majority of the samples that were within a given egg count interval on filter A were within the same interval on duplicate filter B. The counts outside of that interval were never beyond one interval above or below the original counts.

Table II

Mean *Schistosoma haematobium* egg counts of duplicate 5 ml aliquots of 390 urine samples at varying intervals of egg output

| interval | Egg Count A | | Egg Count B | | "t"-test |
|---|---|---|---|---|---|
| | number | mean ± s.e. | number | mean ± s.e. | |
| 0 | 69 | 0 | 72 | 0 | n.s.* |
| 1–9 | 64 | 4.3±0.36 | 69 | 4.7±0.40 | n.s. |
| 10–99 | 104 | 42.8±2.60 | 97 | 44.3±2.49 | n.s. |
| 100–399 | 91 | 208.1±8.44 | 98 | 218.6±9.02 | n.s. |
| 400–1000 | 53 | 664.5±28.26 | 45 | 695.1±28.73 | n.s. |
| >1000 | 9 | 2039.4±586.00 | 9 | 2060.4±588.90 | n.s. |
| TOTAL | 390 | 198.1±22.57 | 390 | 194.5±22.60 | n.s. |

*not significant

Table III

Comparison of *Schistosoma haematobium* egg counts in duplicate 5 ml aliquots of 390 urine samples in terms of the percentage of the aliquots within intervals of egg output

| Egg Count A interval | total | Egg Count B | | | | | |
|---|---|---|---|---|---|---|---|
| | | 0 | 1–10 | 11–99 | 100–399 | 400–1000 | >1000 |
| 0 | 69 | 63 | 6 | | | | |
| 1–9 | 64 | 91%* 9 14% | 9% 49 77% | 6 9% | | | |
| 10–99 | 104 | | 14 13% | 85 82% | 5 5% | | |
| 100–399 | 91 | | | 6 7% | 85 93% | | |
| 400–1000 | 53 | | | | 8 15% | 45 85% | |
| >1000 | 9 | | | | | | 9 100% |

*Egg Count B/Egg Count A × 100.

As an indication of the speed of the test, a team of 10 untrained workers and two individuals previously acquainted with the system were able to obtain urine samples from 200 patients, examine each sample for protein and blood with Bili-Labstix and prepare two 5 ml discs in approximately 2½ hours. The team utilized about 25 disposable syringes and 12 disc holders which had to be cleaned continuously during the survey by thorough washing as described hereinabove. Reading the slides at 40X magnification was rapid with negative filters being scanned in less than 15 seconds, and filters with up to 100 eggs in approximately one minute. Higher counts were time consuming but could be easily controlled by using smaller aliquots of urine. Thus, the average time for preparation and reading of duplicate samples was between one and two minutes.

It will be appreciated that the instant specification and examples are set forth by way of illustration and not limitation, and that various modifications and changes may be made without departing from the spirit and scope of the present invention.

What is claimed is:

1. A process for rapidly ascertaining the presence of Schistosoma eggs in a patient comprising taking a urine sample from the patient, passing about 5 to 10ml of the urine sample through a substantially transparent microporous membrane having a diameter of about 10 to 20mm and pores of a maximum diameter of the order of about 10 $\mu$m, drying the membrane, wetting the membrane with saline solution, viewing substantially the entire membrane under a microscope at a magnification varying from about 25 to 50X, and counting any Schistosoma eggs viewed under the microscope.

2. The process according to claim 1, wherein the urine sample is about 5 ml, and the membrane comprises polycarbonate of a thickness of the order of about 10 $\mu$m, has a diameter of about 13 mm and is viewed under the microscope at a magnitude of about 40X.

* * * * *